(12) United States Patent
Marsh et al.

(10) Patent No.: US 10,603,435 B2
(45) Date of Patent: Mar. 31, 2020

(54) DRIVE MECHANISM FOR USE IN A DRUG DELIVERY DEVICE

(71) Applicant: Sanofi, Paris (FR)

(72) Inventors: William Geoffrey Arthur Marsh, Buckinghamshire (GB); Matthew Meredith Jones, Warwick (GB); Joseph Butler, Rugby (GB); Anthony Paul Morris, West Midlands (GB)

(73) Assignee: Sanofi, Paris (FR)

( * ) Notice: Subject to any disclaimer, the term of this patent is extended or adjusted under 35 U.S.C. 154(b) by 247 days.

(21) Appl. No.: 15/532,432

(22) PCT Filed: Dec. 8, 2015

(86) PCT No.: PCT/EP2015/078962
§ 371 (c)(1),
(2) Date: Jun. 1, 2017

(87) PCT Pub. No.: WO2016/091869
PCT Pub. Date: Jun. 16, 2016

(65) Prior Publication Data
US 2017/0319784 A1    Nov. 9, 2017

(30) Foreign Application Priority Data
Dec. 8, 2014   (EP) .................................. 14306965

(51) Int. Cl.
*A61M 5/20*   (2006.01)
*A61M 5/315*  (2006.01)
*A61M 5/24*   (2006.01)

(52) U.S. Cl.
CPC ........ *A61M 5/2033* (2013.01); *A61M 5/2422* (2013.01); *A61M 5/3157* (2013.01);
(Continued)

(58) Field of Classification Search
CPC .............. A61M 5/2033; A61M 5/2422; A61M 5/31511; A61M 5/31536; A61M 5/31553; A61M 5/31541
See application file for complete search history.

(56) References Cited

U.S. PATENT DOCUMENTS

2002/0007154 A1    1/2002  Hansen et al.
2015/0065963 A1 *  3/2015  Kjeldsen ........... A61M 5/31541
                                                 604/207

FOREIGN PATENT DOCUMENTS

CN         1980705         6/2007
JP         2014-500086     1/2014
(Continued)

OTHER PUBLICATIONS

International Preliminary Report on Patentability in International Application No. PCT/EP2015/078962, dated Jun. 13, 2017, 6 pages.
(Continued)

*Primary Examiner* — Bradley J Osinski
(74) *Attorney, Agent, or Firm* — Fish & Richardson P.C.

(57) ABSTRACT

The disclosure is directed to a drive mechanism for use in a drug delivery device having a cartridge, the mechanism comprising a base element, a toothed piston rod movable from a first retracted position corresponding to a full cartridge to a second extended position corresponding to an empty cartridge, wherein the piston rod is guided within and movable relative to the base portion, and a drive gear having a pinion, which is rotatably held in the base element and in meshed engagement with the toothed piston rod, wherein the toothed piston rod comprises multiple rigid rod pieces which are connected by hinges, and a drive spring, which is fixed to the base element with one end and fixed to the drive gear with another end and which exerts a force or torque to the drive gear for rotating the drive gear relative to the base element, which rotation results in a movement of the toothed (Continued)

piston rod. The drive spring is charged during manufacture or assembly, wherein the energy stored in the drive spring is sufficient to move the piston rod (from the first to the second position. The disclosure is also directed to a drug delivery device.

13 Claims, 11 Drawing Sheets

Specification includes a Sequence Listing.

(52) U.S. Cl.
CPC .... *A61M 5/31511* (2013.01); *A61M 5/31536* (2013.01); *A61M 5/31553* (2013.01); *A61M 5/31585* (2013.01); *A61M 5/31593* (2013.01); A61M 5/2466 (2013.01); A61M 5/31541 (2013.01); A61M 2005/2026 (2013.01); A61M 2005/31518 (2013.01); A61M 2205/581 (2013.01); *A61M 2205/582* (2013.01); *A61M 2205/584* (2013.01); *A61M 2205/585* (2013.01)

(56) References Cited

FOREIGN PATENT DOCUMENTS

| WO | WO 98/01173 | 1/1998 |
|----|----|----|
| WO | WO 2004/078241 | 9/2004 |
| WO | WO 2013/153041 | 10/2013 |
| WO | WO 2013/156224 | 10/2013 |
| WO | WO 2014/052676 | 4/2014 |
| WO | WO 2014/166905 | 10/2014 |

OTHER PUBLICATIONS

International Search Report and Written Opinion in International Application No. PCT/EP2015/078962, dated Feb. 16, 2016, 8 pages.

* cited by examiner

Fig. 4a
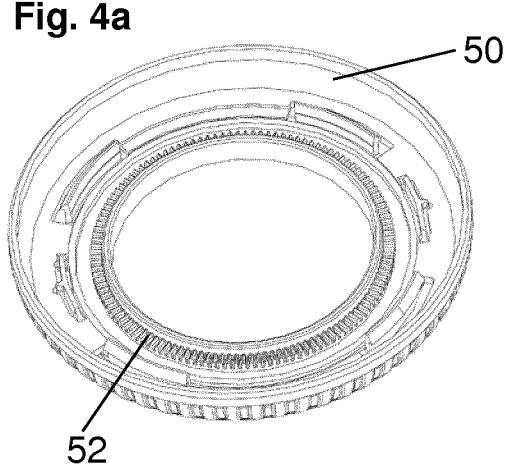
Fig. 4b
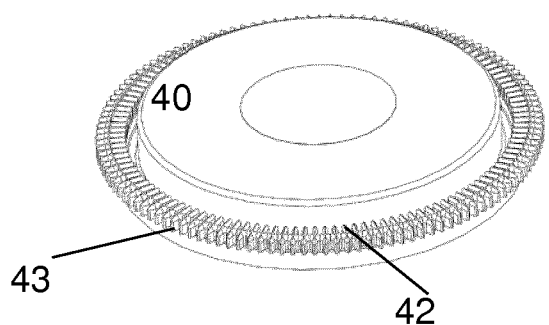
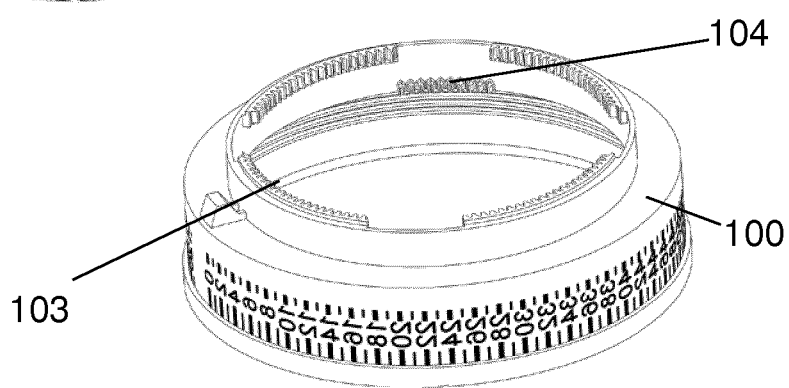
Fig. 4c

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4 (1-39), insulin analogue or
      derivative

<400> SEQUENCE: 1
```

-continued

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20              25              30

Ser Gly Ala Pro Pro Pro Ser
            35
```

DRIVE MECHANISM FOR USE IN A DRUG DELIVERY DEVICE

CROSS REFERENCE TO RELATED APPLICATIONS

This application is a U.S. national stage application under 35 USC § 371 of International Application No. PCT/EP2015/078962, filed on Dec. 8, 2015, which claims priority to European Patent Application No. 14306965.6, filed on Dec. 8, 2014, the entire contents of which are incorporated herein by reference.

TECHNICAL FIELD

The present disclosure is generally directed to a drive mechanism for use in a drug delivery device, i.e. a handheld injection device for selecting and dispensing a number of user variable doses of a medicament.

BACKGROUND

Drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable drug delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. Further types of energy storage may comprise compressed fluids or electrically driven devices with a battery or the like.

These types of delivery devices generally comprise of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the device that is used to set (select) a dose. During an injection, a plunger or piston rod contained within the dose setting mechanism presses against the bung or stopper or piston of the cartridge. This force causes the medication contained within the cartridge to be injected through an attached needle assembly. After an injection, as generally recommended by most drug delivery device and/or needle assembly manufacturers and suppliers, the needle assembly is removed and discarded.

The dosing section of drug delivery devices for selecting and dispensing a number of user variable doses of a medicament often comprises a display for indicating the selected dose to a user. This is especially important where a user may select a different dose each time depending on the state of health. There are mechanical displays, e.g. a drum with printed numbers on its outer surface, wherein the number corresponding to the actually selected dose is visible through a window or opening in the device. Although such mechanical displays are simple and reliable, they usually require a relatively large construction space which makes the devices bulky. In addition, the size of the numbers is in some cases too small for visually impaired users. Further, electronic displays are known, e.g. LCD displays, which have the benefit of a relatively large number size without requiring too much construction space. However, a downside of electronic displays is that they require an energy source and that such electronic components may be too expensive, especially in a disposable drug delivery device.

A disposable drug delivery device is known from WO 2004/078241 A1, wherein the display comprises a number sleeve with numbers printed on its outer surface. The device further comprises a housing, a cartridge holder for retaining a cartridge containing a medicament, a piston rod displaceable relative to the cartridge holder, a driver coupled to the piston rod, a dose setting knob coupled to the driver and fixed to the number sleeve, and an injection button. The number sleeve is in threaded engagement with the housing, such that the number sleeve rotates along a helical path in a first direction during dose selecting and rotates back into the housing in a second, opposite direction during dose dispensing.

It is a problem that injection devices should be small enough to fit into a jacket pocket or a hand bag without difficulty. Also, the injection device must be of a size that enables a piston or the like used to drive the cartridge bung within a cartridge to be moved both to a maximum dispense position. WO 98/01173 A1 discloses a piston rod formed by a tape-like flexible rack. A second embodiment comprises multiple rigid rod pieces connected by hinges. The rigid rod pieces are each provided with curved racks. Supports provided on the opposite side of the racks fit into the cartridge interior to guide the piston rod within the cartridge. It is proposed to drive such a piston rod either by a force applied to the rod end opposite to the cartridge, which requires guiding the rod over its entire length or by a pinion with the piston rod looping around the pinion. Both alternatives result in constraints regarding the design and location of a drive mechanism within a drug delivery device. Such a drive mechanism is suitable for small sized injection devices and enables design choices that are easier to handle for the patient but generally, the patient is still required to set the dose and to charge the device with the energy required for injection. In particular, impaired patients need an injection device that is easy to set and/or to reset in case the wrong dose is set and that is easy to handle in terms of injecting the medication.

SUMMARY

Some embodiments are, in general, applicable for both types of devices, i.e. for disposable devices as well as for reusable devices.

Some embodiments may provide an improved drive mechanism and drug delivery device that requires low operating forces where the dose dispensing, the dose setting and/or the dose cancelling is improved.

A drive mechanism is suitable for use in a drug delivery device with a preferably cylindrical cartridge and comprises a base element which can be referred to as a chassis, a toothed piston rod, which is guided within and movable relative to the base portion or chassis, and a drive gear having a pinion, which is rotatably held in the base element or chassis and in meshed engagement with the toothed piston rod. The toothed piston is movable from a first retracted position that corresponds to a full cartridge to a second extended position that corresponds to an empty cartridge. By moving the piston rod from the first toward the second position when the piston rod is placed behind cartridge bung, the content of the cartridge is dispensed through a dispense interface attached to the opposite end of the cartridge. Although certain aspects are applicable for all of these types of devices, i.e. for devices with or without a drive spring or the like energy storage, the preferred embodiments require some kind of energy storage. The drive spring is charged during manufacture or assembly and the energy stored in the drive spring during said charging is sufficient to move the piston rod from the first to the second position. In other words, the stored energy in the drive spring is sufficient to drive a piston or a bung in the cartridge from an initial position that corresponds to the position of the piston prior to a first use of the cartridge to an end position which corresponds to a completely used cartridge. The energy stored in the spring is sufficient that upon release of the spring, the entire amount of the cartridge can be dispensed over several injection cycles without the need for recharging the drive spring.

The piston rod comprises multiple rigid rod pieces which are connected by hinges, for example integral hinges, such that the rigid rod pieces are arranged in a swiveling manner one behind the other. In the retracted position, at least the major part of the piston rod may be coiled or rolled up inside the device. By means of the pinion, the piston rod is extended segment by segment until in the second position, at least the main part of the piston rod is in an extended condition. The drive mechanism combines the advantages of a small-sized drive mechanism with a very low user input forces required over the entire period of use of the drug delivery device.

The pre-charged or pre-stressed spring can be charged during the assembly, e.g. when the drive spring is connected with the base element or the drive spring can be installed in the drug delivery device in an already pre-stressed state.

The use of a drive spring has the benefit of reducing the user force required to expel the contents of the cartridge and in combination with a flexible piston rod makes a more compact device possible. A pre-charged or pre-stressed spring has the further advantage to reduce the force required during dose setting, because the user is not required to charge the spring with the required dispensing forces to expel the contents of the cartridge. This makes the device user-friendly.

The first position of the piston rod also corresponds to the position of the piston rod after the drug delivery device is assembled during which the piston rod is aligned relative to the bung. The piston rod may also be brought into contact with the bung during manufacturing so that the bung is displaced over a short distance inside the cartridge. This state of the cartridge (ready-to-use after assembly) is also to be understood as a full cartridge.

According to a further embodiment, the rigid rod pieces each comprise a flat plate provided with a straight toothed rack. In other words, neither the rigid rod pieces nor the toothed racks are curved or cambered. This increases the flexural stiffness of the rod and allows use of the rod in a rack and pinion application not requiring that the rod loops around the pinion for extension of the piston rod. Thus, there are more design options for the location and arrangement of the rod and the pinion within a drive mechanism and/or within a drug delivery device. In addition, the pinion may be relatively small, which is not possible when the rod is intended to loop around the pinion.

Typically, the flexible piston rod is located within the base element or chassis and engages, via a rack and pinion interface, the drive gear so that rotation of the drive gear advances the piston rod. When used in a drug delivery device with a cartridge having a bung, the distal end of the piston rod acts on the bung within the liquid medicament cartridge, which expels medicament from the cartridge during dose dispensing by the advancement of the piston rod.

The flexible piston rod is a single component with discrete segments (rigid rod pieces) connected together by thin sections of material which form flexible hinges. The flexibility in bending permits a significantly shorter device format whilst using a conventional glass medicament cartridge.

In a preferred embodiment, the end faces of the segments are planar and, when the flexible piston rod is straightened, the adjacent segment faces abut each other, allowing the component to withstand a compressive load. Together with the design of the segments as flat plates, this contributes to the flexural stiffness of the rod. The flexible piston rod may be restrained within the base element or chassis to maintain the flexed state and prevent the rack gear teeth from disengaging from the pinion of the drive gear. As the piston rod is advanced, via the rack and pinion engagement with the drive gear, the trailing segments of piston rod are drawn into engagement with the drive gear pinion. The subsequent segments drive the preceding segments, loading them in compression, and apply a force to the bung. As the flexible piston rod advances, the first segment may move out of the support provided by the base element or chassis. Without additional support it is likely that the piston rod would buckle under this compressive loading. The additional support to prevent buckling is created by the inner wall of the cartridge providing constraint to the outer surfaces of the flexible piston rod.

To further increase the flexural stiffness of the rod, the flat plate of each segment or rod piece may comprise a flange located on the opposite side of the straight toothed rack. The end faces of the flanges are preferably planar and, when the flexible piston rod is straightened, the adjacent flange faces abut each other, allowing the component to withstand a compressive load. The length of the flanges is preferably adapted to the dimensions of the cartridge such that the flanges (in addition to the plates) guide the rod within the cartridge.

The base element or chassis is a rigid component part, which is typically fixed within a device housing such as a casework or is a part thereof. The base element or chassis is the (immovable) reference for relative movements of the piston rod, the drive gear or further component parts of the drive mechanism or the drug delivery device. The case work may be constituted by jointed components such as an upper casework or housing part and a lower casework or housing part. Preferably, the casework parts comprise clip features to firmly accommodate the components of the drive mechanism and/or to rigidly attach the casework parts to each other.

According to an embodiment, the base element or chassis comprises a first curved guiding section and a second straight guiding section with the drive gear and/or its pinion being arranged protruding into or adjacent to the second straight guiding section. In other words, the meshing engagement between the pinion and the rod segments occurs in the straight guiding section. Thus, the design of the curved guiding section has not to be adapted to allow engagement of the pinion and the rod but may have a form suitable to optimize the available space for storing the flexible piston rod, e.g. in a rolled up state. This drive mechanism allows the design of a relatively compact drug delivery device.

In addition, the base element or chassis may comprise a receiving section for retaining the cartridge. Typically, the receiving section is arranged adjacent to the second straight guiding section such that the rod enters the cartridge shortly after the pinion. The second straight guiding section may lead in or merge into the receiving section. At least one section of the receiving section can have an opening or a window or a transparent section with transparent material so that the user is able the view the cartridge content or the filling level. Further, the bung may be provided with indicators such as a colored marking so that the user can easily recognize the filling level of the cartridge.

In a further embodiment, the base element or chassis has a generally circular configuration with the pinion being located at the center of the base element. The first curved guiding section and the second straight guiding section may be located offset from the centre of the base element. This may contribute in reducing the overall dimensions of the drug delivery device using this drive mechanism.

According to a further embodiment, the drive mechanism comprises a clutch provided by a splined portion of the drive gear and a corresponding splined portion of the base element, wherein the drive gear is axially movable along its rotational axis between a first position in which the drive gear is rotationally constrained to the base element by engagement of the clutch and a second position in which the clutch is disengaged and relative rotation between the base element and the drive gear is allowed. The engagement between drive gear and base element effectively prevents unintended rotation of the drive gear under the action of the torque applied from the pre-charged drive spring, hence the engagement prevents movement of the piston rod prior to delivery of a set dose. Preferably, the splined portions are formed in a radial direction with respect to the axis of rotation of the drive gear. For example, the splined portion of the drive gear may be formed on at least a section of the outer circumferential surface of the drive gear as outer spline features such as teeth and/or grooves and the splined portion of the base element may be formed on at least a section of an inner circumferential surface of the base element as inner spline features such as teeth and/or grooves so that the effective lever arm to prevent relaxation of the drive spring is very effective.

To ensure engagement of the spline features of drive gear and base element, the drive mechanism may comprise a trigger spring such as a compression spring arranged to bias the drive gear into its first position relative to the base element. The trigger spring may be interposed between the base element and the drive gear. In other words, the drive gear and the base element or chassis are decoupled by relative movement of the drive gear and the base element or chassis against the force of the spring. Further, by moving the drive gear into the second position, drive gear and base element are decoupled such that the charged energy of the drive spring can be released and the drive gear is rotated thereby displacing the piston rod.

A further embodiment comprises a trigger, e.g. a dose or actuation button that is axially movable in the direction of the axis of rotation of the drive gear and that is configured to engage and to move the drive gear into the second position relative to the base element when actuated. Actuation of the trigger means that the trigger is moved or pushed axially towards the drive gear by the user such that the clutch between the base element and the drive gear disengages. By engagement with the drive gear, movement of the trigger in the axial direction is transferred to the drive gear which is moved into the second position thereby decoupling the drive gear from the base element. For that purpose, the trigger may be movable between a first axial position and a second axial position, wherein movement of the trigger from the first into the second position decouples the drive gear from the base element. The force required to actuate the button is comparably small, providing a significant ergonomic advantage, particularly for those users with impaired dexterity.

According to a further embodiment, the drive gear comprises at least two separate components that are rotationally fixed and axially movable relative to each other. Thereby, displacement of the drive spring in an axial direction can be effectively avoided, which can affect the efficiency of the drive spring. A further embodiment provides a drive gear with a lower and an upper component. The lower component of the drive gear may contain the pinion that drives the piston rod. The upper component moves axially with the trigger button relative to the lower component. The two parts of the drive gear may be biased apart by the trigger spring which does not add any frictional losses that the drive spring must overcome because both components are rotating together. Preferably, the drive spring is attached to the lower component that is rotationally fixed to the pinion.

According to a further embodiment, the drive gear and the pinion are separate components and the trigger spring is arranged between the pinion and the drive gear. This particularly offers assembly advantages. According to one embodiment, the drive pinion is in the form of an arbor and partly shaped as a cup-like element configured to receive a section of the drive gear. Preferably, the arbor is splined to the drive gear. For that purpose, the inner surface of the cup-like element and the outer surface of the received section of the drive gear are provided with corresponding spline features such as teeth and/or grooves that allow relative axial movement but prevent relative rotation. In particular, the trigger spring ends do not require rotationally sliding contacts. This may also help to ensure that any impact loads generated by the cartridge do not translate into forces on the drive mechanism since the drive spring torque acting on the arbor will absorb the impact energy as the arbor backwinds within angular clearances of the splines.

Preferably, the drive spring is a power spring, often referred to as a "clock" spring or mainspring that preferably provides constant torque. The drive spring may also be a torsion spring. It has been proven effective when the drive spring provides a torque of 51 Nmm when installed.

The drive mechanism may also comprise a setting element, which is rotatable relative to the base element. For that purpose, the setting element can be attached to a housing or at least a casework part of the drug delivery device. Rotation of the setting element relative to the base element is limited by rotational stops defining a zero dose position and preferably also a maximum dose position. The stops may be provided on a housing part or any other suitable element to which the setting element can relatively rotate to. The drive gear is configured to engage the setting element when moved from its first into the second position such that the setting element is rotationally constrained to the drive gear. The drive gear may engage the setting element via a splined interface with splines and/or grooves formed on the drive gear and the setting element, wherein the splined interface permits relative axial movement between the drive gear and the setting element, wherein movement of the drive gear from the first into the second position causes the corresponding spline features on the drive gear and the setting element to engage. In the first position of the drive gear, the setting element is free to rotate relative to the drive gear, while in the second position of the drive gear the setting element is rotationally locked to the drive gear. By rotationally coupling the drive gear to the setting element, rotation of the drive gear is effectively limited. Accordingly, during dispense, the piston rod is driven until the rotational stops engage. The rotational stops may be formed e.g. as protrusions and/or abutments formed on the setting element and a housing part or the chassis. Preferably, the same protrusion defines a zero dose position and a maximum dose position, i.e. the relative rotation between the zero and maximum dose stop is limited to nearly 360°. In particular, by rotation of the setting element in a dose setting process, the user can set the degree of rotation of the drive gear and thus the amount of medicament to be dispensed. The forces required to set the dose are minimal as the drive gear is not engaged with the setting element in its first position.

In addition to non-visual feedbacks, drug delivery devices usually have a display indicating the actually set dose. According to a further embodiment, the setting element is configured as a number wheel provided with a series of marking on an outer circumference. Such number wheel integrates the functions of limiting the rotation of the drive gear and of displaying the set and injected dose in one component, which contributes to the accuracy of the mechanism. A preferred embodiment is based on the idea to provide a series of markings on the outer circumference of the number wheel of the display and to deviate the image of the markings of the number wheel, preferably by 90°, by means of a prism. The outer circumference of the number wheel is an area having enough space to arrange the series of markings with every single figure illustrated, or with every second figure illustrated and a line to mark intermediate positions. On the other hand, as the outer circumference of a wheel might not be the most convenient position of the markings to be readable by a user during dose setting and during dispensing, deviation is provided to increase ease of use.

Regarding the direction of the deviation, it is convenient for some users if the display faces in the direction in which actuation is required during dose setting and/or dose dispensing. For example, if rotation in a plane is required for dose setting and pushing a trigger perpendicular to said plane is required for dose dispensing the display may be arranged next to this plane. Preferably, the number wheel is rotatable about an axis, wherein the prism is arranged such that the image of the markings of the number wheel is deviated in a direction parallel to said axis. According to a preferred embodiment, the at least one prism is a triangular prism, and the series of markings is provided reversed (mirrored) on the outer circumference of the number wheel to be readable through the prism. As an alternative, a penta-prism may be used instead of a simple (triangular) prism allowing the transmission of an image through a right angle without inverting it, that is, without changing the image's handedness. Thus, the series of markings is provided non-mirrored on the outer circumference of the number wheel.

Preferably, the surface of the prism is designed to provide a magnification of the markings on the number wheel. This allows it even with limited space available on the outer circumferential surface of the number wheel to provide an individual figure for every unit (or every second unit) of dose to be set which still is conveniently readable by a user.

A drug delivery device comprises a drive mechanism as described herein. The device may further comprise a housing, which is fixed with the base element, the housing having a longitudinal axis defined by a compartment for receiving the cartridge, wherein the setting element and/or the drive gear is arranged rotatable within the housing with its axis of rotation being perpendicular to the longitudinal axis of the housing.

The drug delivery device may further comprise a dose setting member such as a dose dial for setting user variable doses of a medicament, wherein the dose setting member is rotatable relative to the base element and/or the housing or casework, and wherein the dose setting member and the setting element/number wheel respectively comprise spline features such as teeth and/or grooves configured to engage corresponding spline features such as teeth and/or grooves on the trigger in a first axial position of the trigger such that the trigger rotationally constrains the setting element (number wheel) to the dose setting member (dial), and wherein actuation of the trigger rotationally decouples the dose setting member (dial) and the setting element (number wheel). Actuation of the trigger may cause the spline features of the trigger to disengage from the number wheel so that during dispense, the trigger does not rotate, which is convenient to the user. The dose setting member provides for convenient setting of the dose of medicament, wherein the setting movement of the setting member is directly transferred to the setting element. In other words, by rotating the dose setting member or dial, the user determines the possible degree of rotation of the setting element by setting an angular distance between e.g. a zero dose rotational stop on the housing or the chassis and a respective counter-abutment on the setting element.

According to a further aspect, the drive mechanism further comprises a last dose nut which is guided axially displaceable and non-rotatable with respect to one of the drive gear and the setting element. For example, the nut is rotationally coupled to the drive gear, via a splined interface. It moves along a helical path relative to the setting element (or number wheel), via a threaded interface, when relative rotation occurs between the number wheel and the drive gear (i.e. during dialing). The nut moves towards an end stop, wherein the nut and the end stop may be provided in the drive mechanism of the injection device such that the nut prevents setting of a dose exceeding the (dispensable) amount of a medicament in the injection device. In other words, the end stop preferably defines the length of a track on which the nut travels during dose setting, wherein the length of the track corresponds to the total (dispensable) amount of medicament in the cartridge.

According to a further embodiment, the thread for the last dose nut is provided on an external face of the drive gear and the last dose nut engages an internal surface of the number wheel via splined interface. This embodiment simplifies manufacturing efforts, because it removes the need for spinning a core into the number wheel. Further, the assembly of the drug delivery device is simpler.

According to a further embodiment, the device comprises clicker components. Different clicker mechanisms may be active during dose setting and dose dispensing. For example, a dose setting feedback may be generated by a ratchet provided between the dose setting member and the housing. For that purpose, a clicker element in the form of a flexible arm may be formed on the dose setting element, which overrides a series of protrusions on the housing. Since the dose setting element can be configured to not rotate during dispense, a clear indication for the dose setting process can be provided.

A further embodiment provides for clicker means between the dose setting member and the drive gear, in particular in the axial direction. The drive gear may be provided with teeth extending in an axial direction toward the dose setting member/dial to react against a rigid clicker arm on the dose setting member/dial. As each unit is dialed, the drive gear is forced axially downwards by the depth of the teeth, and then returns to its original axial height under the action of the trigger spring. This causes the audible click as each unit is dialed. In another embodiment, the trigger button is in splined engagement with the dose setting element during dose setting such that the two elements are rotationally constrained but can move axially with respect to each other. The dose setting member has a number of ratchet features such as teeth that extend toward corresponding ratchet elements on the drive gear, preferable on a proximal surface of the drive gear.

According to a further embodiment, a feedback mechanism for generating an audible and/or tactile feedback at the end of dose dispensing is included, the feedback mechanism comprising a flexible clicker on the base element configured to override a protrusion on the setting element to produce an audible and/or tactile feedback, wherein when the drive gear is in the second position, the drive gear engages the clicker arm in such way the effective length of the clicker arm is reduced. By reducing the length of the flexible clicker arm, its stiffness is increased resulting in the increase in volume of the feedback sound.

Preferably, the cartridge contains a medicament when the device is assembled and/or when the drug delivery device is a disposable injection device.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Certain embodiments will now be described in further detail with reference to the accompanying schematic drawings, wherein

FIGS. 4a-c perspective views of different components of the device of FIG. 1;

DETAILED DESCRIPTION

Figure 1:
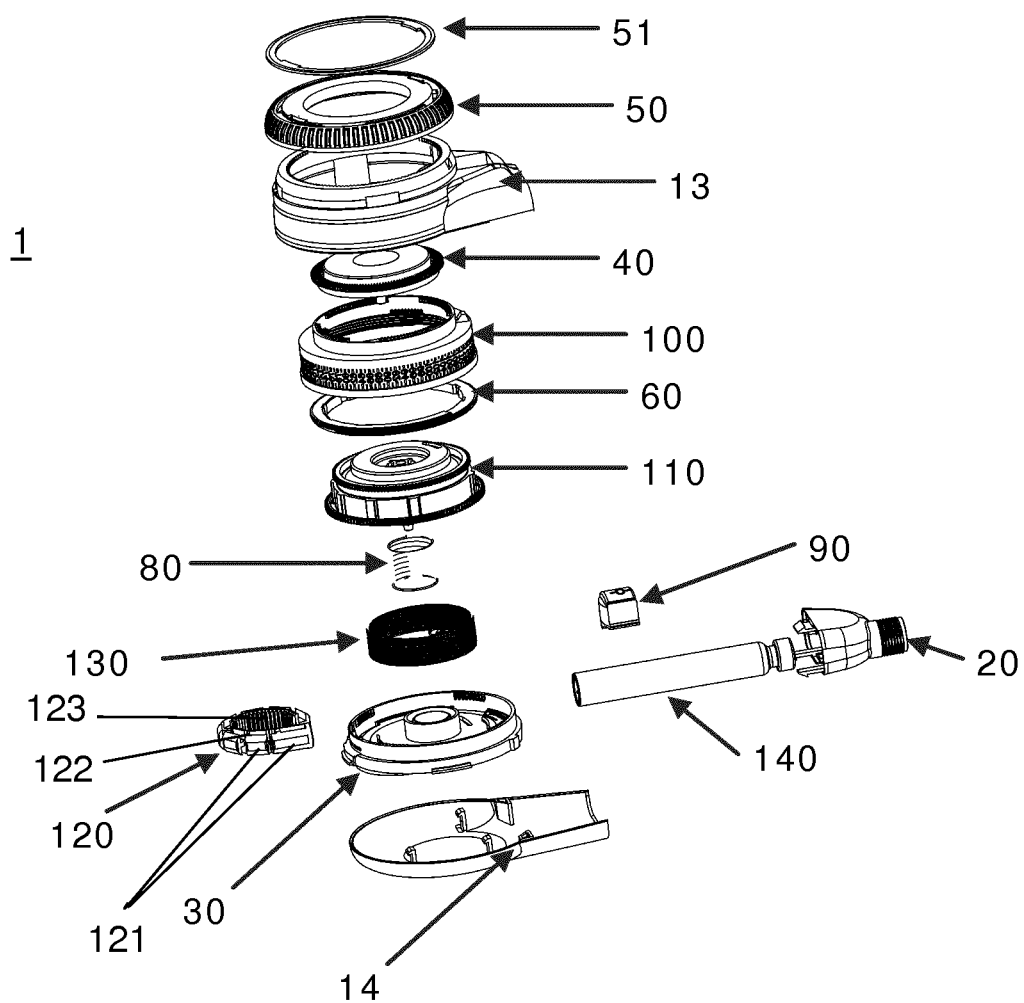
FIG. 1 shows an exploded view of an injection device comprising a drive mechanism.
Figure 2:
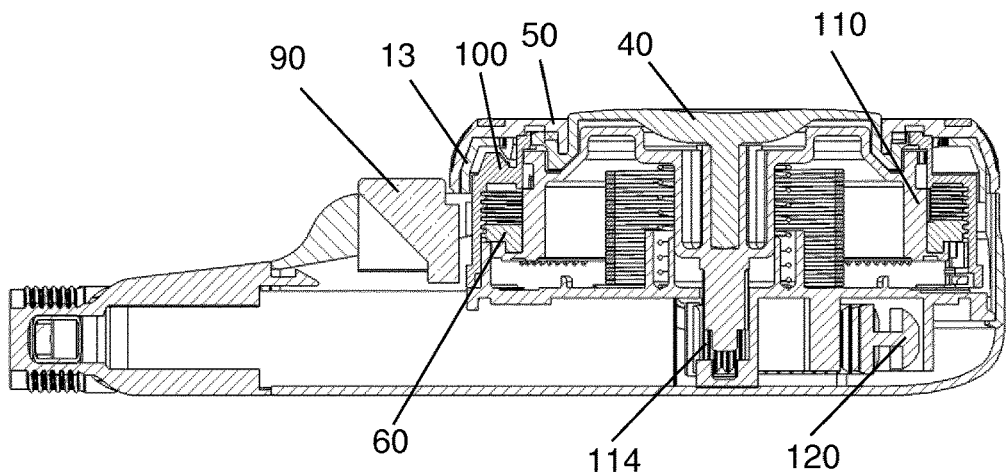
FIG. 2 a cut view of the device of FIG. 1.

FIGS. 1 and 2 show views of the drug delivery device 1. FIG. 1 illustrates the component parts incorporated into the injection device which are a casework 10 or body with an upper or outer casework 13 and a lower casework 14, a cartridge holder 20, a base element or chassis 30, a trigger or dose button 40, a dose setting or dial member 50 with a dial cover 51, a last dose nut 60, a trigger spring 80, a prism 90, a setting element or number wheel 100, a drive gear 110, a flexible piston rod 120, a drive spring 130 and a medicament cartridge 140. The dial cover 51 is rigidly fixed into the dial 50. The upper casework 13 and the lower casework 14 form together the casework 10 of the housing. The upper casework 12 has an opening into which prism 90 is inserted and permanently fixed. Chassis 30 comprises a bearing, which may have the form of a cut open cylinder located at the centre of chassis 30, for receiving the pinion 114 of the drive gear 110.

As shown in FIG. 2, the button 40 is axially constrained between the dial 50 and drive gear 110. The number wheel 100 is axially constrained between the chassis 30 and the upper casework 13. It is free to rotate, relative to the upper casework 13, between two fixed, rotational stops formed by abutments on the number wheel 100 and the upper casework 13.

As the detailed views in FIGS. 4a to 4c of the dial 50 (FIG. 4a), the button (FIG. 4b) and the number wheel (FIG. 4c) show, the button 40 has inner spline/tooth features 42 that interface with corresponding inner spline/tooth features 52 on an inner surface of the dial 50 and spline/tooth features 43 that interface with corresponding spline/tooth features 103 on a radial inner surface of the number wheel 100. These interfaces disconnect during dose delivery. The dial 50 is axially constrained to the casework 10 via retention features (not shown) and is further rotationally constrained, via the splined/tooth interface 52/42, to the button 40 during dose selection. The spline features 103 of the number wheel 100 interact with the button 40 during dialing. Further, on an inner surface, the number wheel 100 also has spline/tooth features 104 that interact with the corresponding drive features of the drive gear 110 during dispense. On the outer circumferential surface, the number wheel is provided with markings that indicate the set dose.

The drive spring 130 is provided in the form of a helical torsion spring and is attached at one end to the chassis 30 and at the other end to the drive gear 110. The drive spring 130 is charged for life, which means that the drive spring is fully charged during assembly and does not require charging by the user until the entire content of the cartridge 140 is dispensed.

The drive gear 110 is axially constrained between the chassis 30 and number wheel 100 and biased away from the chassis 30 by the trigger spring 80 that is provided in the form of a compression spring. It travels axially with the button 40 when the button 40 is pressed to commence dose delivery. During dose selection, the drive gear 110 is in splined engagement with the chassis 30 and hence locked against rotation, but when it travels axially as the button 40 is depressed downwardly for dose delivery this spline engagement is disconnected. Similarly, the separate spline features between the number wheel 100 and the drive gear 110 are engaged when the button 40 is depressed. The trigger spring 80 applies a force between the chassis 30 and drive gear 110 to separate them. In an "at rest" condition, prior to pressing the button 40, this ensures that the drive gear 110 is rotationally coupled to the chassis 30 and that the button splines 42 are engaged with the dial 50.

The flexible piston rod 120 is located within the chassis 30 and is engaged with the drive gear 110 via a rack and pinion interface so that counter-clockwise (CCW) rotation of the drive gear 110 advances the flexible piston rod 120 towards a bung in the cartridge 140. The pinion 114 is rotatably held in the chassis 30 and is in meshed engagement with the piston rod 120. The piston rod 120 is a single component with discrete rigid rod pieces or segments 121 connected together by thin sections of material which form flexible hinges 122. The end faces of the segments 121 are planar and, when the piston rod 120 is straightened the adjacent segment faces abut each other, allowing the component to withstand a compressive load. Segments 121 are shaped as a flat plate provided with rack teeth 123 on one side and a flange on the opposite side. The segment facing towards the cartridge comprises a pressure foot for contacting the cartridge bung. As the piston rod 120 is advanced, via the rack 123 and pinion 114 engagement with the drive gear 110, the trailing segments 121 of piston rod 120 are drawn into engagement with the drive gear pinion 114. The subsequent segments 121 drive the preceding segments, loading them in compression, and apply a force to the bung. As the piston rod 120 advances, the first segment moves out of a support provided by the chassis 30. Without additional support it is likely that the piston rod 120 would buckle under this compressive loading. The additional support to prevent buckling is created by the inner side wall of the cartridge 140 providing constraint to the outer surfaces of the piston rod 120.

The distal end of the flexible piston rod 120 acts on a bung within the liquid medicament cartridge. The liquid medicament cartridge 140 is housed within the cartridge holder 20. The cartridge holder 20, chassis 30 and outer/upper casework 13 and lower casework 14 and the prism 90 are fixed rigidly relative to one another.

The drug delivery device can be operated to deliver a number of user variable doses of medicament from the cartridge 140, via a needle (not shown). The device is disposable and is delivered to the user in a fully assembled condition ready for use. The mechanism provides separate user interfaces for setting and delivery of a dose. In short terms, a dose is set by rotating dial 50 located on the face of the device. Delivery of a dose is initiated by pressing dose button 40, positioned in the centre of the dial 50, and dose delivery will continue while the dose button 40 remains depressed, until the complete set dose has been delivered. The mechanism provides audible, visual and tactile feedback, all three on the setting and delivery of each dose. Any dose size can be selected between zero and a pre-defined maximum, in increments to suit the medicament and user profile. The mechanism permits cancelling of a dose without any medicament being dispensed by rotation of the dial 50 in the opposing direction to when selecting a dose.

The force required to actuate the dose button 40 and the distance which it has to move are small, providing a significant ergonomic advantage, particularly for those users with impaired dexterity. The mechanism requires consistent user input forces to set a dose and initiate the delivery of a dose, which are insensitive to variations in the force required to displace the bung within the cartridge 140. The dial 50 is disengaged during dose delivery so that it does not rotate, which improves handling of the device during use. The device has relatively low part count, very compact size and is particularly attractive for cost sensitive device applications.

In the following use and function of the device will be described in more detail.

Figure 3:
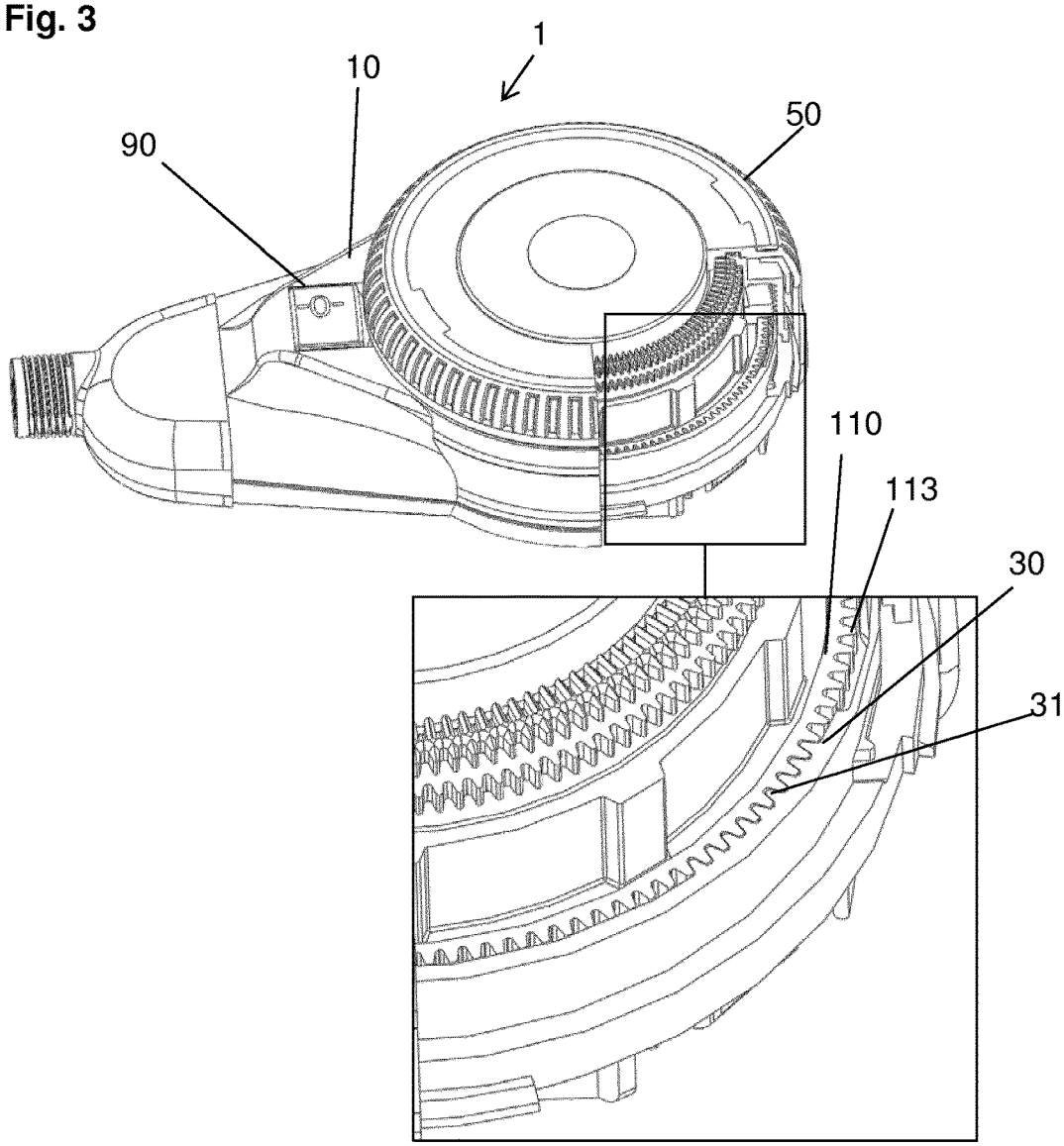
FIG. 3 a perspective view of the device of FIG. 1 with parts removed.

FIG. 3 shows the device 1 in the 'at rest' condition. Dose marking '0' on the number wheel is visible through the prism 90. The drive spring, which is fully charged during assembly of the device or which is pre-wound, applies a torque to the drive gear 110 when zero dose units are dialed. The drive gear 110 is prevented from rotating, under the action of this torque, by a clutch mechanism formed by the spline interface with the chassis 30. As shown in the enlarged extract of FIG. 3, the splined interface comprises outer spline/tooth features 113 on an outer circumferential surface of the drive gear 110 that engage with inner spline/tooth features 31 on an inner circumferential surface of the chassis 30. By relative axial displacement, the drive gear 110 and the chassis 30 can be decoupled so that the drive gear 110 can rotate under the force of the drive spring.

Figure 5:
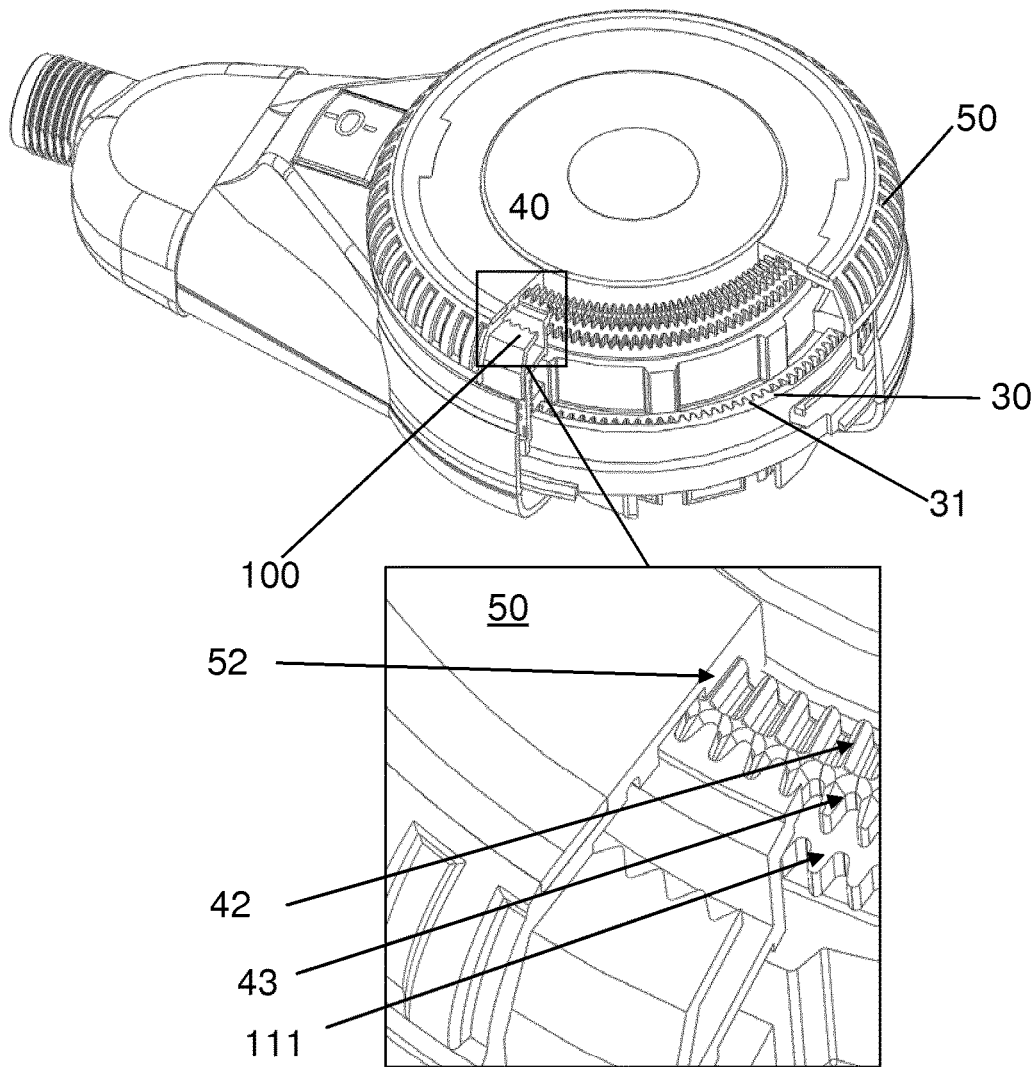
FIG. 5 a perspective view of the device of FIG. 1 with parts removed.
Figure 6:
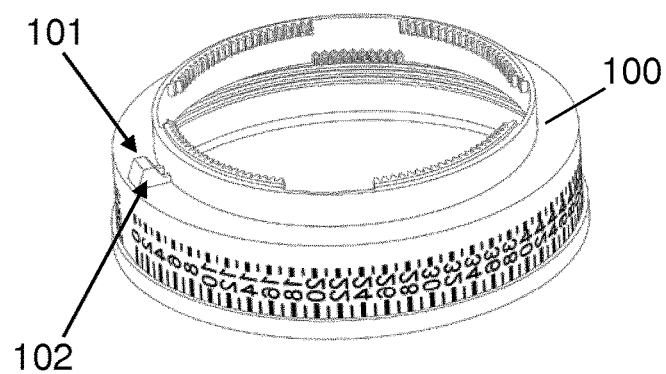
FIG. 6 a perspective view of the number wheel.

To dial a variable dose of liquid medicament, the user rotates the dial 50 in clockwise (CW) direction. The spline features provided on the underside of the dial, and on the button and the number wheel are engaged (see FIG. 4). FIG. 5 shows the spline interfaces during dose dialing. As the enlarged section of FIG. 5 illustrates, rotation of the dial 50 generates an identical rotation in the button 40 due to the spline interface 52/42 between the button 40 and the dial 50. Further, because of the spline interface 43/103 between the button 40 and the number wheel 100, the number wheel 100 is also caused to rotate. The drive gear 110 is prevented from rotating due to the engagement of its splined teeth 113 with the splined teeth 31 of the chassis 30 (see FIG. 3). As shown in FIG. 6, the number wheel 100 has two fixed rotational stops, namely a maximum dose stop 101 and a zero dose stop 102 formed by an abutment. On an inner surface of the upper casework, respective counter abutments are provided. CW rotation of the dial 50 rotates the number wheel 100 away from a zero unit stop formed by said counter abutment on the casework 13 and towards a maximum unit stop formed as a counter abutment surface on the upper casing 13. The dial 50 can be rotated by the user in both CW and CCW directions when the number wheel 100 is not in contact with the zero dose or maximum dose stop abutments in the casework 13. The zero unit abutment 102 prevents CCW rotation of the dial 50 below the zero unit position. The maximum dose abutment 101 prevents setting of a dose greater than the mechanism maximum.

Figure 7:
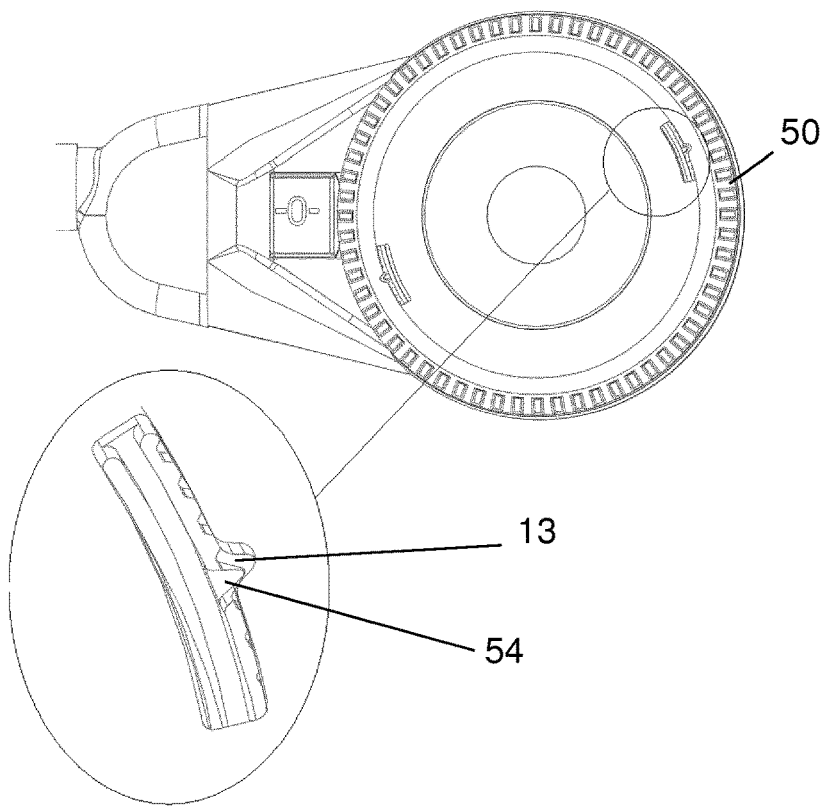
FIG. 7 a top view of the device of FIG. 1.

In FIG. 7, a top view of the drive mechanism is shown, where the dial 50 is provided with a dial clicker 54 in the form of a flexible arm that clicks against a series of protrusions on the upper casework 13. The clicker 54 is hidden from view of the user by the dial cap 51 which clips onto the dial 50. Since during dose delivery the dial 50 does not move, the dial 54 clicker only operates during dialing of a dose. The dial clicker 54 biases the number wheel relative to the prism through the dial 50 ensuring that only whole units of medicament are dialed.

Figure 8:
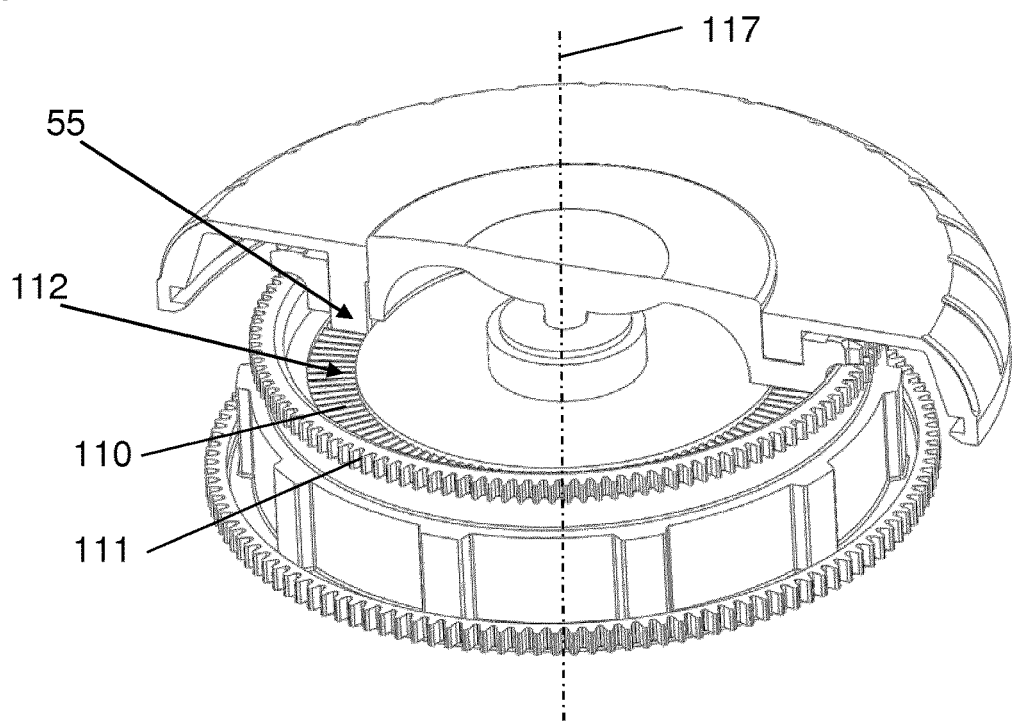
FIG. 8 a perspective view of parts of the drive mechanism in accordance with a further embodiment.

In FIG. 8, an alternative of the clicker mechanism is presented. This clicker mechanism works axially between the dial 50 and the drive gear 110. Helical teeth 112 on the drive gear 110 may react against a rigid clicker arm 55 on the dial 50. As each unit is dialed by rotating the dial 50 around the axis of rotation 110 of the drive gear 110, the drive gear is forced axially downwards by the depth of the teeth 112, and then returns to its original axial height under the action of the trigger spring. This causes the audible click as each unit is dialed. During delivery, the dial clicker 55 is disengaged through the axial travel of the button 40 and drive gear 110 moves away from the dial 50. This embodiment is advantageous in terms of robustness as the metal spring is likely to be more robust than a plastic arm. In addition, multiple contact faces can be used to spread the load more evenly, reducing damage, without increasing the torque required to overcome the clicker. FIG. 8 also shows that the outer circumferential surface of the drive gear 110 is generally provided with the two sets of splined teeth 111 and 113, wherein the first set 111 is for engagement with correspondingly formed spline features 104 on the number wheel and wherein the second set 113 is provided for engagement with the chassis 30.

Figure 9:
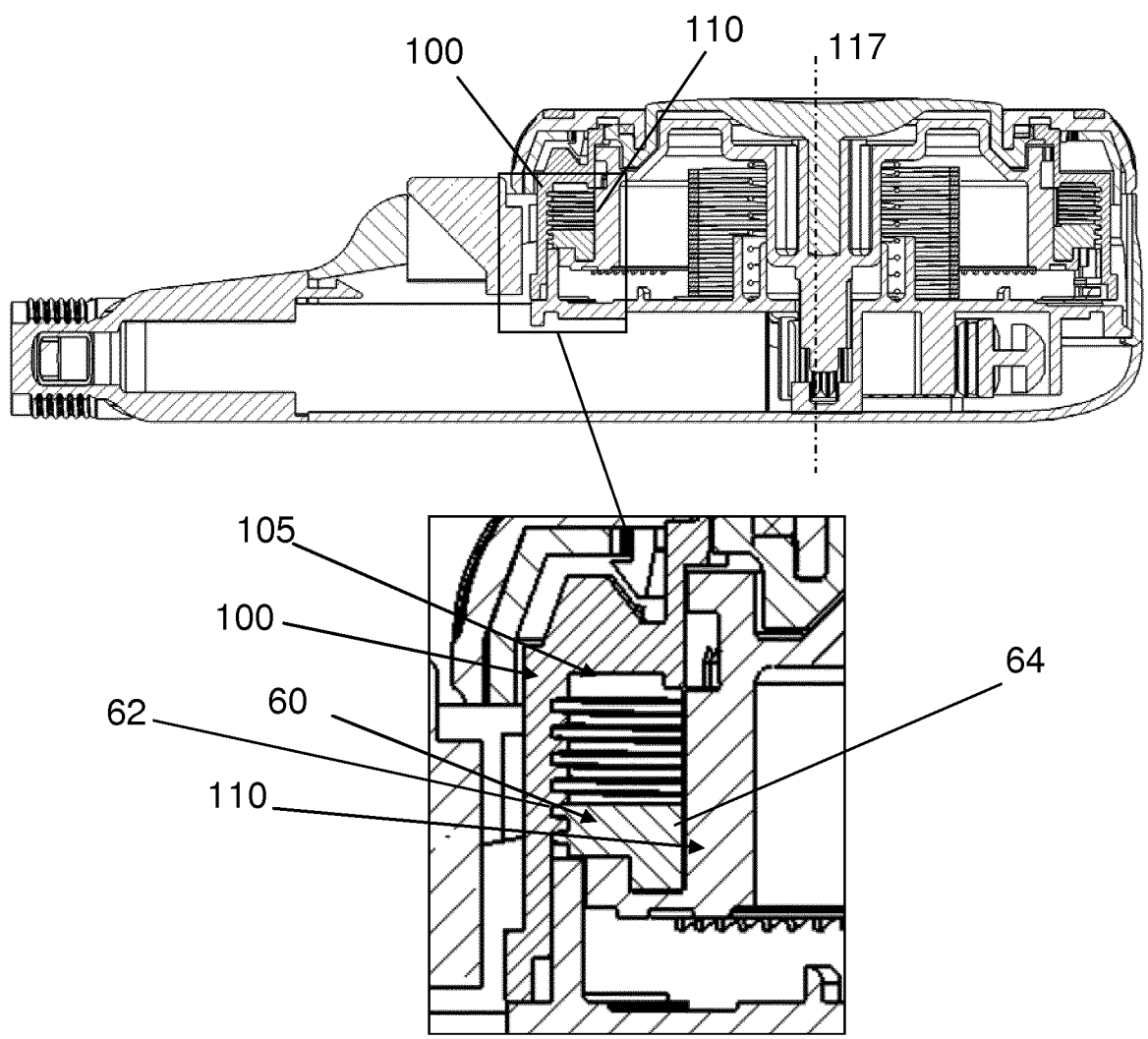
FIG. 9 the last dose nut mechanism of the device of FIG. 1 in a cut view.

In FIG. 9, the last dose mechanism is displayed. The last dose nut 60 is located between the number wheel 100 and the drive gear 110. It is rotationally coupled to the drive gear 110 via a splined interface 64 provided on a radial inner surface of the last dose nut 60 and on a radial outer surface of the drive gear 110 that enables relative axial displacement but prevents relative rotation. For example, the splined interface 64 may include axially extending ribs on the radial inner surface of the last dose nut 60 that engage in respective axially extending grooves on the radial outer surface of the drive gear 110. Further, the last dose nut 60 is engaged with the number wheel 100 by a thread engagement wherein the last dose nut is provided with a helically extending groove forming an outer thread 62 engaging a helically extending counterpart in the number wheel so that the last dose nut 60 moves along a helical path relative to the number wheel 100 when relative rotation occurs between the number wheel 100 and the drive gear 110 (i.e. during dialing). Relative rotation of the number wheel 100 and the drive gear 110 around the rotational axis 117 causes the last dose nut 60 to travel axially towards the last dose abutment 105 (end stop) on the number wheel 100. Depending on how many units have already been delivered by the mechanism, during selection of a dose, the last dose nut 60 may contact its last dose abutment 105. The abutment prevents further relative rotation of the number wheel 100 and the drive gear 110, and therefore limits the dose that can be selected. The position of the last dose nut 60 is determined by the total number of relative rotations between the number wheel 100 and drive gear 110, which have occurred each time the user sets a dose. With the mechanism in a state in which a dose has been selected, the user is able to deselect any number of units from this dose. Deselecting a dose is achieved by the user rotating the dial 50 CCW. The relative rotation between the number wheel 100 and the drive gear 110 causes the last dose nut 60 to return axially, away from the last dose abutment 105.

Figure 10A:
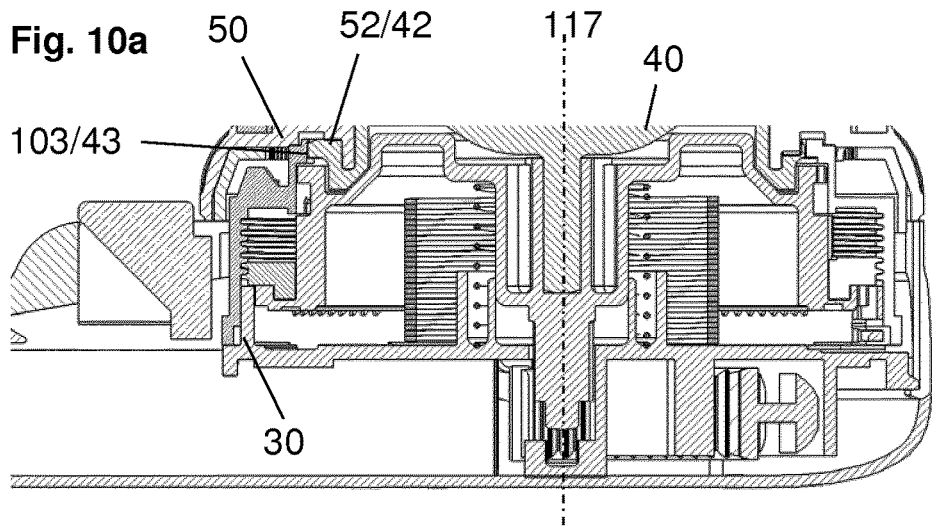
FIGS. 10a-c a dispense sequence of the drive mechanism of the device of FIG. 1 in a cut view.
Figure 10B:
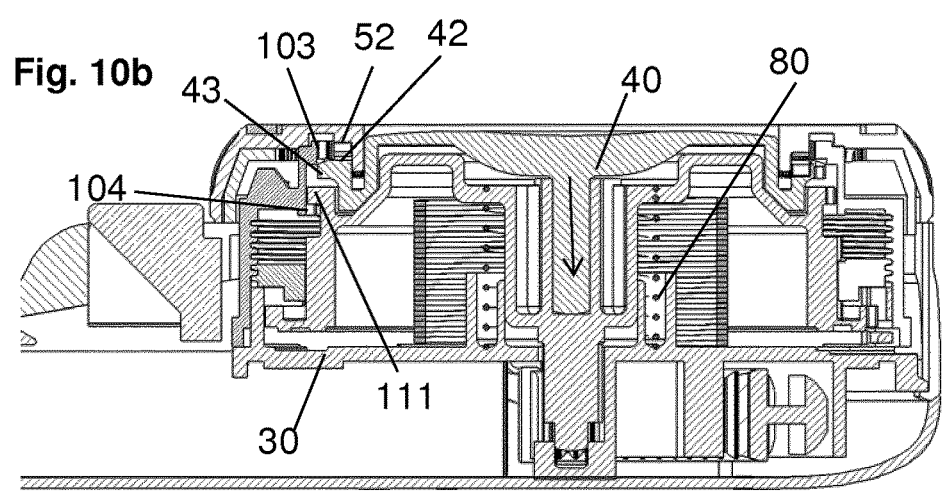
Figure 10C:
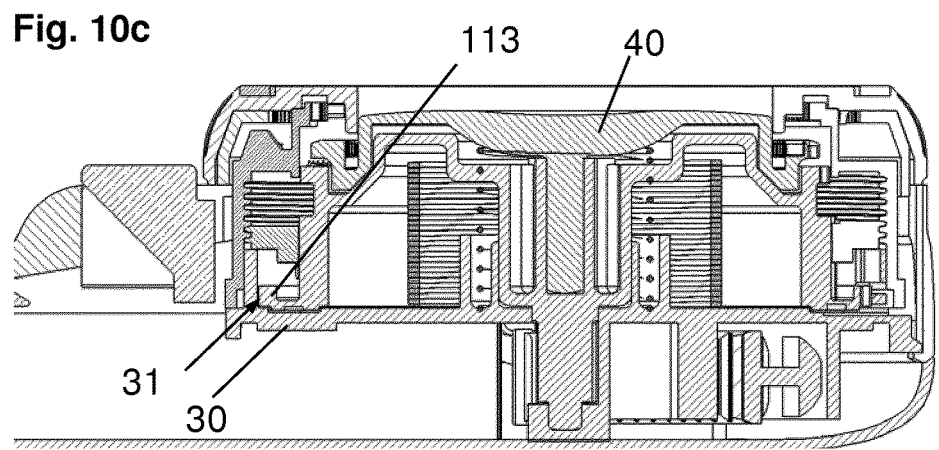

In FIGS. 10a to 10c, a sequence in the drive mechanism to dispense a dose is shown. FIG. 10a shows the device after a dose has been dialed. The zero stop abutment on the number wheel has been rotated away from its counter-abutment. The button 40 is engaged with the number wheel 100 via the spline interface 43/103 and the dial is engaged with the button 40 via the spline interface 52/42. When the button 40 is depressed in an axial direction along the axis of rotation 117, the button 40 moves relative to the dial 50 and the number sleeve 100 so that the button 40 disengages from the spline features 52 of the dial 50 and disengages from the spline features 103 from the number wheel 100.

The drive gear 110 moves axially with the button 40 against the force of the trigger spring 80, and when the button 40 is partially depressed (FIG. 10b), the drive gear 110 engages the splined teeth 111 on its outer circumferential surface with the spline features 104 on the number wheel 100. As the button is fully depressed (FIG. 10c), the drive gear 110 disengages from the chassis locking teeth or spline feature 31 and is now able to rotate relative to the chassis 30. In other words, the drive gear 110 is movable from a first 'at rest' to a second actuated position where the drive gear is disengaged from the chassis 30.

After the button 40 is fully depressed, the drive gear 110 and the number wheel 100 are rotationally locked and free to rotate under the action of the drive spring 130. The button 40 is disengaged from all spline teeth and therefore the mechanism can rotate relative to the button 40 and the dial 50.

The pinion 114 of the drive gear 110 acts on the teeth of the piston rod 120 causing the medicament to be dispensed. At the end of dose, the number wheel 100 zero stop abutment stops against the stop feature in the outer casework 13 causing the mechanism to stop. During delivery of a dose, the drive gear 110 and the number wheel 100 rotate together, so that no relative motion in the last dose nut 60 occurs.

The dose delivery clicker arm is a compliant cantilever beam integrated into the chassis 30, which interfaces axially with ratchet features on the drive gear 110 (not shown). The ratchet teeth spacing corresponds to the drive gear 110 rotation required to deliver a single dose unit. During dispense, as the drive gear 110 rotates, the ratchet features engage with the clicker arm to produce an audible click with each dose unit delivered.

When the button 40 is released, the trigger spring 80 causes the drive gear 110 and hence the button 40 to travel axially to their at-rest position. This travel causes the drive gear 110 spline teeth 113 to mesh with the chassis 30 again, locking the drive gear 110 against further rotation. The drive gear 110 also disengages its spline teeth 111 from the number wheel 100. The button 40 then re-engages its spline teeth features 42 and 43 with the dial 50 and the number wheel 100. The user is then free to dial their next dose when required.

Figure 11:
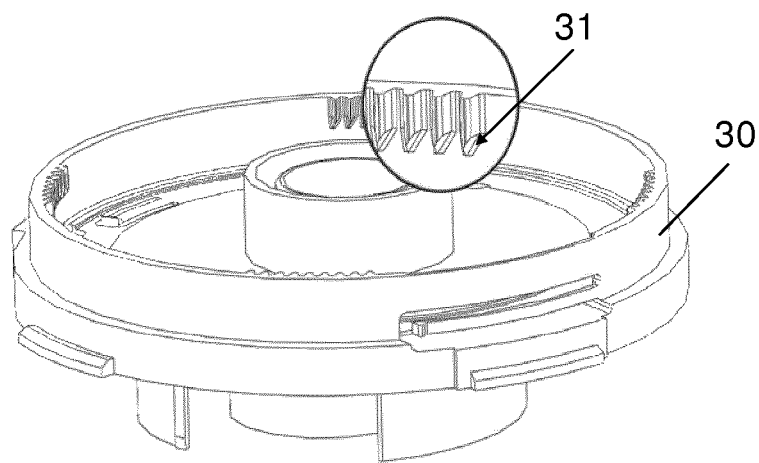
FIG. 11 a perspective view of the base element in accordance with a further embodiment.

In FIG. 11, a further embodiment is shown in which the spline teeth on the chassis are angled or have an angled face on their lower surface so that when the button 40 is released, the re-engagement of the spline teeth 31 fractionally back-winds the drive gear 110 thereby removing the engagement of the number wheel 100 to the zero dose stop abutment. Alternatively, the angled spline teeth may be provided on the dial gear 110. The angled features removes the effect of clearances in the mechanism (for example due to tolerances) which could otherwise lead to slight advancement of the piston rod and medicament dispense when the device is dialed for the subsequent dose, due to the number wheel zero dose stop no longer restraining the mechanism and instead the restraint returning to the splines between the drive gear and the chassis.

Figure 12A:
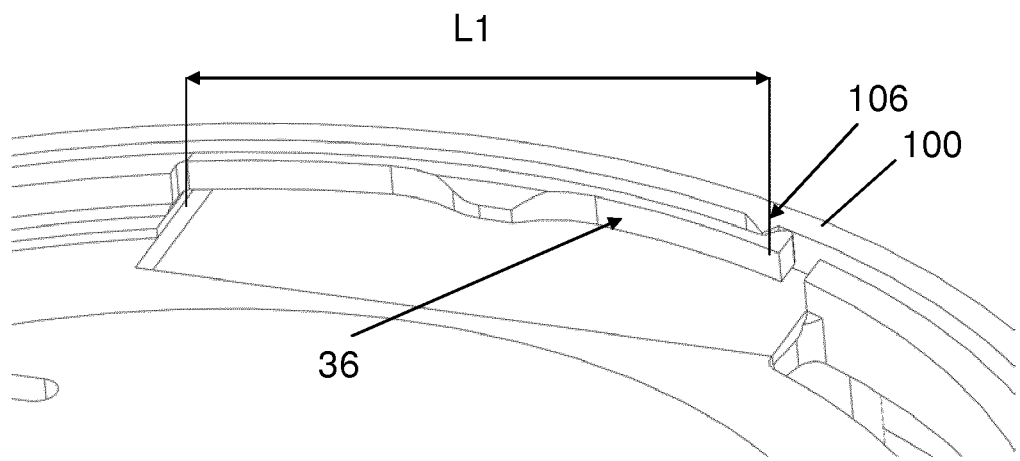
FIGS. 12a-b parts of the drive mechanism in accordance with a further embodiment in a perspective view.
Figure 12B:
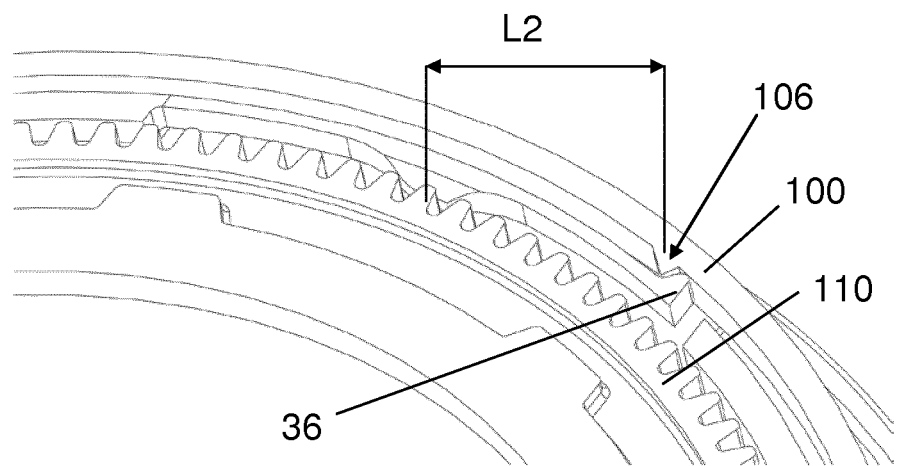

In FIGS. 12a and 12b a mechanism to indicate the end of dose is shown. The end of dose mechanism produces an audible click at the end of dose when the mechanism reaches its zero position. The click is created by interaction between a flexible clicker arm 36 on the chassis 30, the drive gear 110 and the number wheel 100. The volume of the click increases during dose delivery and is likely to be masked by the dial clicker when the user dials the device to or from zero. With respect to FIG. 12a, during dialing, the button 40 and the drive gear 110 are spaced axially away from the chassis 30, and the flexible clicker arm 36 is able to over-ride the protrusion 106 on an inner diameter of the number wheel 100 with minimum torque due to its large effective cantilever length L1 and therefore the volume of the audible click will be low. During dose delivery, when the button 40 and hence drive gear 110 are pushed axially towards the chassis 30, the inner surface of the clicker arm 36 contacts the drive gear 110 when the arm over-rides the bump feature or protrusion 106 of the number wheel 100. This contact with the drive gear 110 reduces the effective length of the clicker arm to L2 (FIG. 12*b*), thereby increasing its stiffness which leads to an increase in the volume of the audible click produced when the dose returns to zero.

Figure 13:
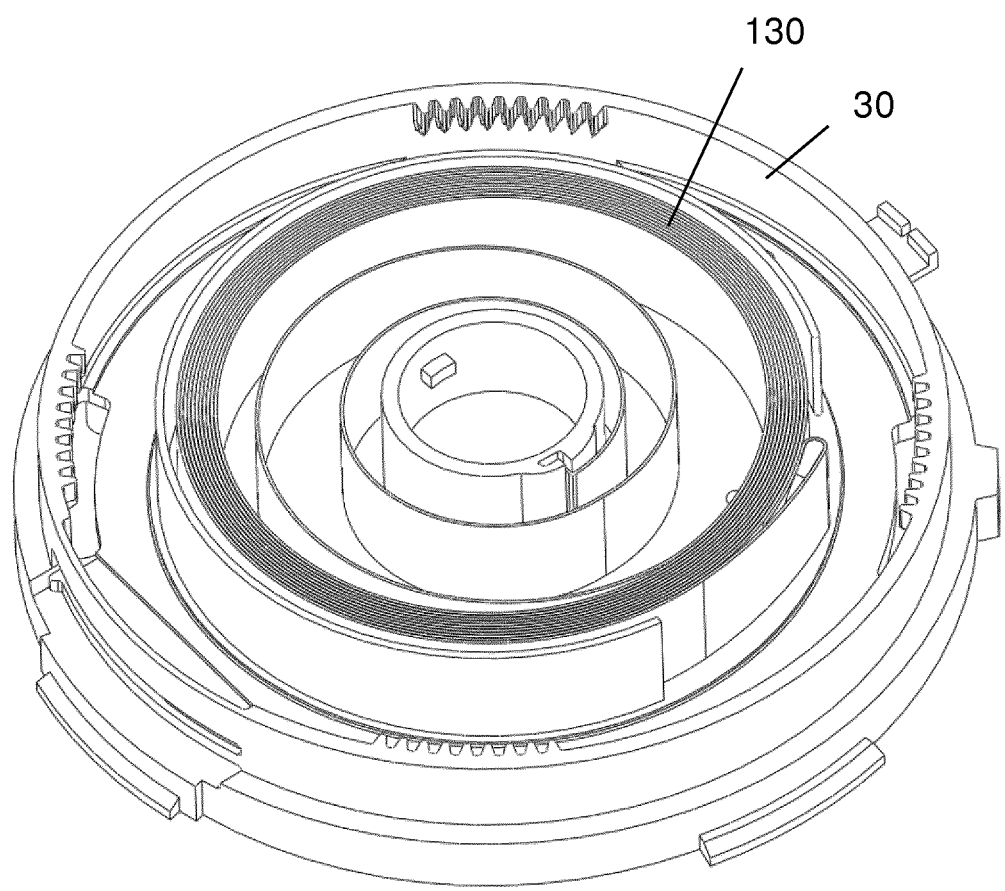
FIG. 13 parts of the drive mechanism in accordance with a further embodiment in a perspective view.

Instead of a torsion spring, a power spring may be assembled. FIG. 13 is a perspective view of the device with a power spring fitted on the chassis. When using a torsion spring as the drive spring 130, the end-form of the spring can be fixed to the drive gear that moves axially when the button is pressed. The small amount of button travel and hence axial travel of drive gear 110 does not have a significant effect on the performance of the torsion spring. However, in particular when using a power spring, it may be beneficial that the inner end-form of the spring does not move axially with the drive gear. To implement this feature, another embodiment includes a drive gear that is split into two components that are rotationally fixed but that can move axially relative to each other.

Figure 14:
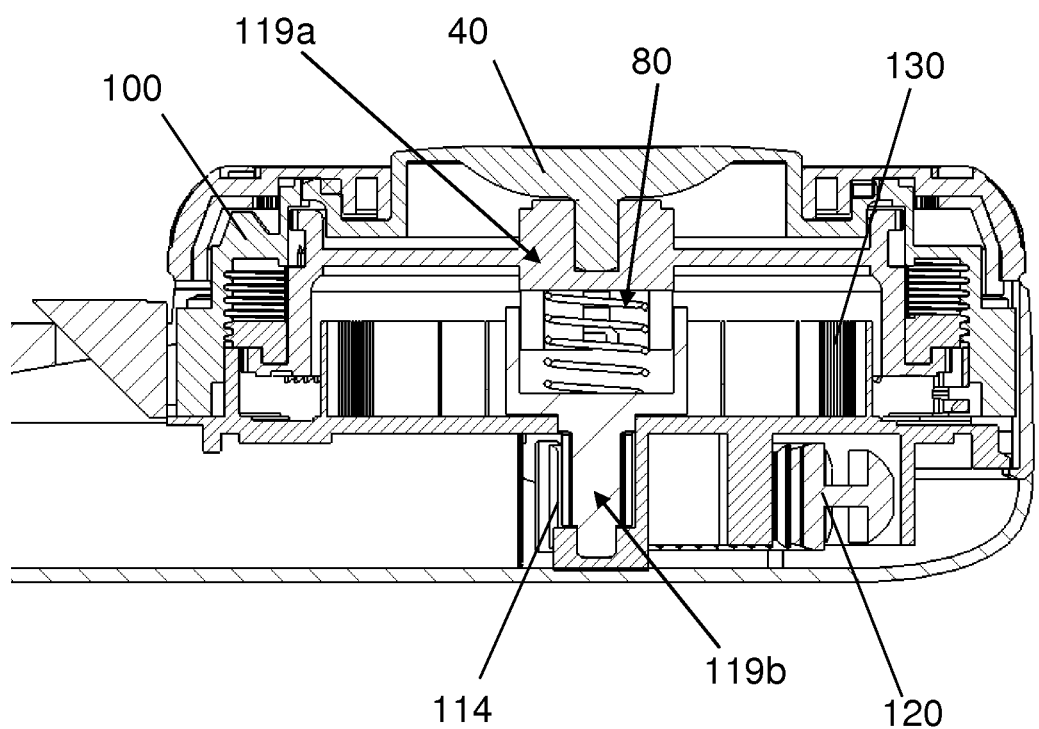
FIG. 14 parts of the drive mechanism in accordance with a further embodiment in a cut view.

The embodiment shown in FIG. 14 includes a drive gear that includes two separate components that are rotationally fixed and axially movable relative to each other by spline engagement. The upper first drive gear component 119*a* constitutes the engagement section with the number wheel 100 and is also urged by the button 40 in downward direction during dispense. On a central section on the underside of the first drive gear component 119*a*, the protruding section of the first drive gear component 119*a* is received in an opening of the lower second drive gear component 119*b*. The components 119 and 119*b* interface by way of a spline connection formed on the outer diameter of the protruding section and on an inner diameter of the receiving section (opening) so that relative axial movement is possible like a telescope but relative rotation between the first drive gear component 119*a* and the second drive gear component 119*b* is prevented. The trigger spring 80 is arranged in said opening between the first drive gear component 119*a* and the second drive gear component 119*b*.

The lower component 119*b* does not move axially and secures the inner leg of the power spring 130. It also contains the pinion 114 that drives the flexible piston rod 120. The upper drive gear component 119*a* moves axially with the button travel relative to the second drive gear component 119*b* and interfaces with the number wheel 100 and the last dose nut 60. Alternatively, the pinion 114 may be part of an arbor that constitutes the second component. The two parts 119*a* and 119*b* are biased apart by the trigger spring 80, which also gives the advantage that during dose delivery, since both components are rotating together, the spring does not add any frictional losses that the drive spring 130 must overcome. When the button is actuated, which means that the button 40 is moved in downward direction so that the clutch between the drive gear 110 and the number wheel 100 is released, the trigger spring is compressed.

REFERENCE NUMERALS 1 drug delivery device
10 body (casework)
13 upper casework
14 lower casework
20 cartridge holder
30 chassis (base element)
31 spline teeth
36 clicker arm
40 dose button
42 spline teeth
43 spline teeth
50 dial (dose setting member)
51 dial cover
52 spline teeth
54 dial clicker
55 dial clicker
60 last dose nut
62 outer thread
64 splined interface
80 trigger spring
90 prism
100 number wheel (setting element)
101 maximum stop
102 zero stop
103 spline teeth
104 spline teeth
105 end stop
106 protrusion
110 drive gear
111 spline teeth
112 helical teeth
113 spline teeth
114 pinion
117 Axis of rotation of drive gear
119*a* first drive gear component
119*b* second drive gear component
120 flexible piston rod
121 segment (rigid rod piece)
122 hinge
123 rack teeth
130 drive spring
140 cartridge

The invention claimed is:

1. A drive mechanism for use in a drug delivery device having a cartridge, the drive mechanism comprising:
    a base element;
    a toothed piston rod movable from a first retracted position corresponding to the cartridge being full to a second extended position corresponding to the cartridge being empty, wherein the toothed piston rod is guided within and movable relative to the base element; and
    a drive gear having a pinion rotatably held in the base element and in meshed engagement with the toothed piston rod, wherein the toothed piston rod comprises multiple rigid rod pieces connected by hinges;
    a drive spring fixed to the base element with one end and fixed to the drive gear with another end, the drive spring configured to exert a force or torque to the drive gear for rotating the drive gear relative to the base element to move the toothed piston rod, wherein the drive spring is charged during manufacture or assembly, wherein energy stored in the drive spring is sufficient to move the toothed piston rod from the first retracted position to the second extended position, and
    a clutch provided by a splined portion of the drive gear and a corresponding splined portion of the base element, wherein the drive gear is axially movable along its rotational axis between a first position in which the drive gear is rotationally constrained to the base element by engagement of the clutch and a second position in which the clutch is disengaged and relative rotation between the base element and the drive gear is allowed.

2. The drive mechanism according to claim 1, wherein the drive gear comprises at least two separate components that are rotationally fixed and axially movable relative to each other.

3. The drive mechanism according to claim 1, wherein the drive gear is axially displaceable and rotationally fixed with respect to the pinion.

4. The drive mechanism according to claim 1, wherein a compression spring is arranged between the pinion and the drive gear.

5. The drive mechanism according to claim 1, wherein the drive spring is a power spring or a torsion spring.

6. The drive mechanism according to claim 1, further comprising a compression spring arranged to bias the drive gear into its first position relative to the base element.

7. The drive mechanism according to claim 6, further comprising a trigger being axially movable in a direction of an axis of rotation of the drive gear, wherein actuation of the trigger results in an axial movement of the drive gear into its second position.

8. The drive mechanism according to claim 1, further comprising a setting element rotatable relative to the base element, wherein rotation of the setting element relative to the base element is limited by rotational stops defining a zero dose position and a maximum dose position; and wherein the drive gear is configured to engage the setting element when moved from the first position to the second position such that the setting element is rotationally constrained to the drive gear.

9. The drive mechanism according to claim 8, wherein the setting element is configured as a number wheel provided with a series of markings on an outer circumference of the number wheel.

10. A drug delivery device comprising
    a cartridge;
    a drive mechanism comprising:
        a base element,
        a toothed piston rod movable from a first retracted position corresponding to the cartridge being full to a second extended position corresponding to the cartridge being empty, wherein the toothed piston rod is guided within and movable relative to the base element, and
        a drive gear having a pinion rotatably held in the base element and in meshed engagement with the toothed piston rod, the drive gear being movable between a first position and a second position, wherein the toothed piston rod comprises multiple rigid rod pieces which are connected by hinges; and
    a drive spring fixed to the base element with one end and fixed to the drive gear with another end, the drive spring configured to exert a force or torque to the drive gear for rotating the drive gear relative to the base element to move the toothed piston rod, wherein the drive spring is charged during manufacture or assembly, wherein energy stored in the drive spring is sufficient to move the toothed piston rod from the first position to the second position;
    a dose setting member for setting user variable doses of a medicament, the dose setting member being rotatable relative to the base elements;
    a setting element rotatable relative to the base element, wherein the dose setting member and the setting element respectively comprise spline features configured to engage corresponding spline features on a trigger in a first axial position of the trigger such that the trigger rotationally constrains the setting element to the dose setting member; and
    a feedback mechanism generating an audible and/or tactile feedback at an end of dose dispensing, the feedback mechanism comprising a flexible clicker arm on the base element configured to override a protrusion on the setting element to produce the audible and/or tactile feedback, wherein when the drive gear is in the second position, in which relative rotation between the drive gear and the base element is allowed, the drive gear engages the flexible clicker arm in such way that an effective length of the flexible clicker arm is reduced.

11. The drug delivery device according to claim 10, wherein movement of the trigger from the first axial position into a second axial position rotationally decouples the trigger from the dose setting member and the setting element.

12. The drug delivery device according to claim 10, wherein the cartridge contains a medicament.

13. The drug delivery device according to claim 10, wherein the drug delivery device is a disposable injection device.

* * * * *

UNITED STATES PATENT AND TRADEMARK OFFICE
CERTIFICATE OF CORRECTION

PATENT NO. : 10,603,435 B2  
APPLICATION NO. : 15/532432  
DATED : March 31, 2020  
INVENTOR(S) : William Geoffrey Arthur Marsh et al.

Page 1 of 1

It is certified that error appears in the above-identified patent and that said Letters Patent is hereby corrected as shown below:

On the Title Page

On page 2, Column 1, item (57), (Abstract), Line 3, delete "(from" and insert -- from --

In the Claims

In Column 21, Line 34, Claim 1, delete "position," and insert -- position; --

Signed and Sealed this  
Thirteenth Day of October, 2020

Andrei Iancu  
*Director of the United States Patent and Trademark Office*